US009475770B2

(12) United States Patent
Huntley et al.

(10) Patent No.: US 9,475,770 B2
(45) Date of Patent: Oct. 25, 2016

(54) LOW-TEMPERATURE SYNTHESIS OF METHYLPHENIDATE HYDROCHLORIDE (75) Inventors: C. Frederick M. Huntley, East Greenwich, RI (US); Erik Wayne Kataisto, West Warwick, RI (US); Knicholaus Dudley La Lumiere, Groton, CT (US); Helge Alfred Reisch, Westerly, RI (US)

(73) Assignee: Rhodes Technologies, Coventry, RI (US)

( * ) Notice: Subject to any disclaimer, the term of this patent is extended or adjusted under 35 U.S.C. 154(b) by 319 days.

(21) Appl. No.: 13/994,393

(22) PCT Filed: Dec. 16, 2011

(86) PCT No.: PCT/IB2011/003140
§ 371 (c)(1),
(2), (4) Date: Oct. 28, 2013

(87) PCT Pub. No.: WO2012/080834
PCT Pub. Date: Jun. 21, 2012

(65) Prior Publication Data
US 2015/0038720 A1 Feb. 5, 2015

Related U.S. Application Data (60) Provisional application No. 61/424,424, filed on Dec. 17, 2010.

(51) Int. Cl.
C07D 211/68 (2006.01)
C07D 211/34 (2006.01)

(52) U.S. Cl.
CPC .................................. C07D 211/34 (2013.01)

(58) Field of Classification Search
CPC ..................................................... C07D 211/34
USPC ......................................................... 546/238
See application file for complete search history.

(56) References Cited

U.S. PATENT DOCUMENTS

| | | | |
|---|---|---|---|
| 2,507,631 A | 5/1950 | Hartmann et al. | |
| 2,838,519 A | 6/1958 | Rometsch | |
| 2,957,880 A | 8/1960 | Rometsch | |
| 4,347,374 A | 8/1982 | Kollonitsch et al. | |
| 5,733,756 A | 3/1998 | Zeitlin et al. | |
| 5,936,091 A | 8/1999 | Khetani et al. | |
| 6,121,453 A | 9/2000 | Zavareh | |
| 6,242,464 B1 | 6/2001 | Harris et al. | |
| 2005/0080111 A1 | 4/2005 | Bayne et al. | |
| 2005/0124640 A1 | 6/2005 | Cardozo et al. | |
| 2005/0171155 A1 | 8/2005 | Krsek et al. | |
| 2006/0135777 A1 | 6/2006 | Trafelet et al. | |
| 2010/0179327 A1 | 7/2010 | Haar, Jr. et al. | |

FOREIGN PATENT DOCUMENTS

| | | |
|---|---|---|
| WO | WO 98/25902 A1 | 6/1998 |
| WO | WO 01/27070 A1 | 4/2001 |
| WO | WO 2005/012291 A1 | 2/2005 |
| WO | WO 2008/022396 A1 | 2/2008 |
| WO | WO 2008/087190 A2 | 7/2008 |
| WO | WO 2010/080787 A1 | 7/2010 |
| WO | WO 2011/067783 A1 | 6/2011 |

OTHER PUBLICATIONS

Decomposition "wiseGREEK" p. 1 (2003).*
Abdu-Allah, H.H.M., et al., "Design, Synthesis, and Structure—Affinity Relationships of Novel Series of Sialosides as CD22-Specific Inhibitors," *J. Med. Chem.* 51:6665-6681, American Chemical Society (2008).
Brinkmann, T., et al., "Reaction of aspartic acid derivatives with Grignard reagents—synthesis of γ,γ-disubstituted α- and β-aminobutyrolactones," *Tetrahedron: Asymmetry* 11:3827-3836, Elsevier Science Ltd. (2000).
Byrne, C.J. and Ward, A.D., "A Facile Porphyrin Esterification / Etherification Procedure," *Tetrahedron Letters* 29 (12):1421-1424, Pergamon Press plc (1988).
Deutsch, H.M., et al., "Synthesis and Pharmacology of Potential Cocaine Antagonists. 2 Structure—Activity Relationship Studies of Aromatic Ring-Substituted Methylphenidate Analogs," *J. Med. Chem.* 39:1201-1209, American Chemical Society (1996).
Horgan, S.W., et al., "Process Development in the Synthesis of the ACE Intermediate MDL 28,726," *Organic Process Research & Development* 3: 241-247, American Chemical Society and The Royal Society of Chemistry (1999).
International Search Report for International Application No. PCT/IB2011/003140, European Patent Office, Netherlands, mailed on Feb. 28, 2012.
Keller, F., et al., "Compounds Related to Carnitine: Derivatives of 4-Dimethylamino-3-hydroxybutyric Acid," *J. Med. Chem* 6:202-203, American Chemical Society (1962).
Kondo, N., et al., "Cadystin A and B, Major Unit Peptides Comprising Cadmium Binding Peptides Induced in Fission Yeast—Separation, Revision of Structures and Synthesis," *Tetrahedron Letters* 25(35):3869-3872, Pergamon Press Ltd. (1984).
Prashad, M., et al., "Enzymatic resolution of (±)-*threo*-methylphenidate," *Tetrahedron: Asymmetry* 9:2133-2136, Elsevier Science Ltd. (1998).
Prashad, M., et al., "The First Enantioselective Synthesis of (2R,2'R)-*threo*-(+)-Methylphenidate Hydrochloride," *J. Org. Chem* 64:1750-1753, American Chemical Society (1999).
Van Hijfte, V., et al., "A Versatile Entry into the Synthesis of α-(Monofluoromethyl) Amino Acids : Preparation of α-(Monofluoromethyl) Serine and (E)-Dehydro-α-(monofluoromethyl) Ornithine," *Tetrahedron Letters* 34 (30):4793-4796, Pergamon Press Ltd. (1993).

(Continued)

*Primary Examiner* — Celia Chang
(74) *Attorney, Agent, or Firm* — Sterne, Kessler, Goldstein & Fox PLLC (57) ABSTRACT

The present invention describes a process for the preparation of methylphenidate hydrochloride. The process involves the esterification of ritalinic acid and methanol in the presence of an acid catalyst at a low temperature. The process may optionally involve the addition of an orthoester.

33 Claims, 4 Drawing Sheets

(56) References Cited

OTHER PUBLICATIONS

Zoeller, J.R., "Thermal Ring Annulation of α-Vinylcinnamate Methyl Esters. A Method for the Generation of 3,4-Diyhydro-2-naphthoate and 2-Naphthoate Methyl Esters," *J. Org. Chem.* 53:4716-4719, American Chemical Society (1988).

Eckerman, D.A., et al., "Enantioselective Behavioral Effects of *threo*-Methylphenidate in Rats," *Pharmacology Biochemistry & Behavior 40*:875-880, Pergamon Press, United Kingdom (1991).

Markowitz, J.S., et al., "Advances in the Pharmacotherapy of Attention-Deficit-Hyperactivity Disorder: Focus on Methylphenidate Formulations," *Pharmacotherapy 23(10)*:1281-1299, Wiley-Blackwell, United States (2003).

\* cited by examiner

FIGURE 1

| Entry | Time (h) | 1.57 M | | | 3.13 M | | |
|---|---|---|---|---|---|---|---|
| | | 25 °C | 40 °C | 60 °C | 25 °C | 40 °C | 60 °C |
| 1 | 0 | 0.57 | 0.57 | 0.57 | 0.58 | 0.58 | 0.58 |
| 2 | 24 | 0.34 | 1.04 | 4.68 | 1.05 | 3.01 | 8.64 |
| 3 | 48 | 0.6 | 1.65 | 7.69 | 1.62 | 4.27 | 9.95 |
| 4 | 72 | 0.59 | 1.92 | 7.74 | 1.51 | 4.92 | 10.71 |

LOW-TEMPERATURE SYNTHESIS OF METHYLPHENIDATE HYDROCHLORIDE

BACKGROUND OF THE INVENTION

1. Field of the Invention

The present invention describes a process for the preparation of methylphenidate hydrochloride. The process involves the esterification of ritalinic acid and methanol in the presence of an acid catalyst at a low temperature. The process may optionally involve the addition of an orthoester.

2. Related Art

Methylphenidate (MPD) and methylphenidate hydrochloride are therapeutic agents that are widely used for the treatment of children with attention-deficit hyperactivity disorder. Methylphenidate contains two chiral carbon atoms and thus, four isomers of methylphenidate are possible as shown in Scheme 1. Early formulations contained all four isomers, d-threo methylphenidate, l-threo methylphenidate, d-erythro methylphenidate, and l-erythro methylphenidate. Markowitz, J. S., et al., *Pharmacotherapy* 23:1281-1299 (2003). The erythro isomers were subsequently removed from the formulations due to their association with adverse effects.

excreted into the urine as the de-esterified metabolite, dl-threo ritalinic acid. Patrick, K. S., *J. Med. Chem.* 24:1237-1240 (1981).

Synthetic methods for preparing racemic mixtures of threo- and erythro-α-phenyl-2-piperidineacetamides as raw materials for the preparation of threo methylphenidate are described in U.S. Pat. Nos. 2,507,631; 2,838,519; 2,957,880; and 5,936,091; and in PCT International Patent Publication No. WO 01/27070. These methods include using sodium amide as base in the nucleophilic substitution of chlorine in 2-chloropyridine with phenylacetonitrile, followed by hydrolysis of the formed nitrile and reduction of the pyridine ring to a piperidine ring by hydrogenation on $PtO_2$ catalyst to obtain erythro-enriched α-phenyl-2-piperidineacetamide, which is then subjected to epimerization, hydrolysis, and esterification of threo-ritalinic acid. Alternatively, 2-bromopyridine can be used instead of 2-chloropyridine. Deutsch, H. M., et al., *J. Med. Chem.* 39:1201-1209 (1996).

Several methods have been described in the literature for preparing the d-threo enantiomer of methylphenidate. An enzymatic resolution is described in U.S. Pat. No. 5,733,756. A recrystallization/crystallization method, as well as an Scheme 1 enzymatic resolution, are disclosed in PCT International Patent Publication No. WO 98/25902.

U.S. Pat. No. 2,957,880 describes a sequence involving the resolution of the amide derivative of the corresponding erythro isomer, conversion to the threo isomer, followed by the hydrolysis of the amide to the corresponding acid, and esterification of the resulting acid with methanol. In U.S. Pat. No. 6,242,464, the d-threo enantiomer is prepared by resolving racemic threo methylphenidate employing a di-aroyltartaric acid, preferably a ditoluoyltartaric acid. In U.S. Pat. No. 6,121,453, the d-threo enantiomer is prepared by resolving racemic threo methylphenidate employing (–)-menthoxyacetic acid.

Prashad, M., et al., *Tetrahedron: Asymmetry* 9:2133-2136 (1998) describes the esterification of ritalinic acid in methanol with hydrogen chloride gas at 45-50° C. for 16 hours. Treatment of the free base with hydrogen chloride gas followed by crystallization afforded d-threo methylphenidate hydrochloride in 16% yield.

Prashad, M., et al., *J. Org. Chem.* 64:1750-1753 (1999) describes the esterification of tert-butyloxycarbonyl pro- Until the introduction of d-threo methylphenidate hydrochloride, (dexmethylphenidate hydrochloride, Focalin®) in 2002, all marketed forms of methylphenidate contained a 50:50 racemic mixture of d-threo methylphenidate and l-threo methylphenidate in the form of the hydrochloride salt (Ritalin®, Concerta®, Metadate®, and Methylin®). In 2007, a transdermal patch containing racemic dl-threo methylphenidate (Daytrana®) was approved by the FDA.

The attention-deficit hyperactivity disorder psychotherapeutic effects, as well as the undesired pressor and anorexic actions, reside primarily in the d-enantiomer. Eckerman, D. A., et al., *Pharmacol. Biochem. Behav.* 40:875-880 (1991). However, in view of the recent efforts to develop l-threo-methylphenidate as an antidepressant, the l-threo-methylphenidate isomer of racemic formulations may not necessarily represent a passive component. Rouhi, A. M., *Chem. Eng. News* 81:56-61 (2003).

Methylphenidate is metabolized primarily by de-esterification to the inactive metabolite ritalinic acid (RA). About 60-81% of the oral dose of dl-threo methylphenidate is tected d-threo ritalinic acid in methanol with the addition of hydrogen chloride gas at 50° C. for 15 hours. From this reaction, d-threo methylphenidate hydrochloride was obtained in 70% yield.

U.S. Patent Application Publication No. 2005/0171155 describes the esterification of dl-ritalinic acid in about 20 molar equivalents of methanol saturated with hydrogen chloride gas under reflux. From the reaction, dl-threo methylphenidate hydrochloride was obtained in 37% yield.

U.S. Patent Application Publication No. 2006/0135777 describes the esterification of d-threo ritalinic acid hydrochloride with methanol by means of thionyl chloride in toluene and dimethylformamide as catalyst in a two-step exothermic process. The crude product was purified to afford the desired d-threo methylphenidate hydrochloride in 73% yield.

U.S. Patent Application Publication No. 2010/0179327 describes the preparation of amino acid esters such as methylphenidate. The reference describes the reaction of threo-α-phenyl-α-(2-piperidinyl)acetic acid, methanolic HCl, and trimethyl orthoacetate with heating at reflux (temperatures above 60° C.) to form methylphenidate. Conversion rates of 91.7 to 98.5% and yields of 42.2 to 95.0% are reported.

A need exists for a more practical and economical process for esterification of ritalinic acid to methylphenidate hydrochloride.

BRIEF SUMMARY OF THE INVENTION

In one embodiment, the present invention provides a method for preparing methylphenidate or a salt thereof, which comprises:
reacting:
(a) ritalinic acid or a salt thereof; and
(b) methanol;
(c) in the presence of an acid catalyst;
in a reaction mixture at a reaction temperature of less than 45° C. to obtain a product mixture comprising methylphenidate or a salt thereof.

In one embodiment, the salt of ritalinic acid is threo ritalinic acid hydrochloride.

In one embodiment, the salt of methylphenidate is threo methylphenidate hydrochloride.

In one embodiment, the acid catalyst is hydrogen chloride.

In one embodiment, the reaction temperature is less than 45° C., preferably less than 43° C., more preferably less than 42° C., and most preferably less than 40° C. In another embodiment, the reaction temperature is in the range from about 10° C. to about 45° C., or from about 10° C. to about 43° C., or from about 10° C. to about 42° C., or from about 10° C. about 40° C.; or from about 20° C. to about 45° C., or from about 20° C. to about 43° C., or from about 20° C. to about 42° C., or from about 20° C. to about 40° C., or from about 20° C. to about 30° C.; or from about 30° C. to about 45° C., or from about 30° C. to about 43° C., or from about 30° C. to about 42° C., or from about 30° C. to about 40° C.; or from about 35° C. to about 45° C., or from about 35° C. to about 43° C., or from about 35° C. to about 42° C., or from about 35° C. to about 40° C.

In one embodiment, the ratio of ritalinic acid:methanol is from about 1:10 to about 1:100 molar equivalents. In another embodiment, the ratio of ritalinic acid hydrochloride:methanol is from about 1:9 to about 1:86 molar equivalents.

In one embodiment, the ratio of ritalinic acid:acid catalyst is from about 1:1.1 to about 1:9 molar equivalents. In another embodiment, the ratio of ritalinic acid hydrochloride:acid catalyst is from about 1:0.1 to about 1:8 molar equivalents.

In another embodiment, the present invention provides a method for preparing methylphenidate or a salt thereof, according to the reaction described above, which further comprises:
(d) adding, after commencing the reaction, an orthoester of the formula wherein
$R^2$ is hydrogen or alkyl; and
$R^3$ is selected from the group consisting of alkyl, haloalkyl, cycloalkyl, aryl, and aralkyl.

In one embodiment, $R^3$ is alkyl, preferably methyl.

In one embodiment, the orthoester is trimethyl orthoformate. In another embodiment, the orthoester is trimethyl orthoacetate.

In one embodiment, the method further comprises including a co-solvent that does not chemically interfere with the reaction in the reaction mixture. In certain embodiments, the co-solvent is selected from the group consisting of acetates, ketones, ethers, aromatic solvents, and higher alkanes, such as $C_{4-20}$ linear or branched alkanes, preferably $C_{5-10}$ linear or branched alkanes. In certain embodiments, the co-solvent is selected from the group consisting of methyl acetate, ethyl acetate, isopropyl acetate, n-butyl acetate, isobutyl acetate, acetone, methyl ethyl ketone, methyl isobutyl ketone, tetrahydrofuran, 2-methyltetrahydrofuran, acetonitrile, methyl t-butyl ether, dibutyl ether, cyclopentyl methyl ether, anisole, toluene, xylene, heptanes, and mixtures thereof.

In one embodiment, the orthoester is added after about 95% conversion, or after about 98% conversion, or after about 99% conversion of the ritalinic acid or salt thereof to the methylphenidate or salt thereof.

In one embodiment, the ratio of ritalinic acid:orthoester is from about 1:1.1 to about 1:10 molar equivalents, and preferably from about 1:1.1 to about 1:6 molar equivalents.

In another embodiment, the ratio of ritalinic acid hydrochloride:orthoester is from about 1:0.1 to about 1:9 molar equivalents, and preferably from about 1:0.9 to about 1:5 molar equivalents.

In another embodiment, a polish filtration of the batch is performed after addition of the orthoester.

In another embodiment, the method for preparing methylphenidate or a salt thereof, as described above, further comprises isolating said methylphenidate or salt thereof from the product mixture. The methylphenidate or salt thereof may be isolated using standard techniques to cause the methylphenidate or salt thereof to precipitate out of solution, such as: (i) by cooling the product mixture, (ii) by adding a solvent in which the methylphenidate or methylphenidate salt has reduced solubility to the product mixture, (iii) by removing at least a portion of the methanol or methanol co-solvent mixture from the product mixture, by (iv) adding a crystallization seed to the product mixture, or (v) by a combination of any of (i) to (iv).

In one embodiment, said isolating step is carried out by adding to the product mixture a solvent in which the methylphenidate or methylphenidate salt has reduced solubility (i.e., an anti-solvent), which solvent is selected from the group consisting of acetates, ketones, ethers, aromatic solvents, and higher alkanes, such as $C_{4-20}$ linear or branched alkanes, preferably $C_{5-10}$ linear or branched alkanes. Non-limiting examples of such solvents may be selected from the group consisting of ethanol, isopropanol, n-propanol, n-butanol, iso-butanol, t-amyl alcohol, cyclopentanol, methyl acetate, ethyl acetate, isopropyl acetate, n-propyl acetate, n-butyl acetate, isobutyl acetate, acetone, methyl ethyl ketone, methyl isobutyl ketone, tetrahydrofuran, 2-methyltetrahydrofuran, acetonitrile, diethyl ether, methyl-t-butyl ether, dibutyl ether, cyclopentyl methyl ether, anisole, toluene, xylene, hexanes, heptanes, and mixtures thereof.

In another embodiment, said isolating step is carried out by removing at least a portion of the reaction solvent present (for example, methanol with or without a co-solvent) in the product mixture simultaneous with adding the aforementioned solvent.

In another embodiment, said isolating step is carried out by removing at least a portion of the reaction solvent (for example, methanol without or without a co-solvent) prior to adding the aforementioned solvent.

DETAILED DESCRIPTION OF THE INVENTION

The present invention provides a process for esterifying ritalinic acid and methanol in the presence of an acid catalyst. It has been discovered that the use of low temperature in the esterification reaction provides unexpectedly high conversions and yields in a reaction mixture which is stable. A stable reaction mixture does not show significant hydrolysis back to ritalinic acid over an extended period of time (i.e., 50 hours or longer).

The term "low-temperature" denotes a temperature of less than 45° C., preferably less than 43° C., more preferably less than 42° C., and most preferably less than 40° C. The term "low-temperature" may also denote a temperature in the range of from about 10° C. to about 45° C., preferably from about 10° C. to about 43° C., more preferably from about 10° C. to about 42° C., even more preferably from about 10° C. to about 40° C.; or from about 20° C. to about 45° C., preferably from about 20° C. to about 43° C., even more preferably from about 20° C. to about 42° C., even more preferably from about 20° C. to about 40° C., and most preferably from about 20° C. to about 30° C.; or from about 30° C. to about 45° C., preferably from about 30° C. to about 43° C., more preferably from about 30° C. to about 42° C., even more preferably from about 30° C. to about 40° C.; or from about 35° C. to about 45° C., preferably from about 35° C. to about 43° C., more preferably from about 35° C. to about 42° C., even more preferably from about 35° C. to about 40° C. The invention process is carried out in this temperature range, which is "low" compared to known esterification processes that typically proceed at reflux (temperatures above 60° C.) or at temperatures close to reflux (about 50° C. to about 60° C.).

The term "about" is used herein to mean the given number plus or minus 1 to 10%.

The term "salt" as used herein is meant to encompass all salts of the disclosed compounds. Examples of salts include inorganic and organic salts. For example, salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, citric, edetic, edisylic, estolic, esylic, formic, fumaric, glucceptic, gluconic, glutamic, glycolic, glycolylarsanilic, hexamic, hexylresorcinoic, hydrabamic, hydrobromic, hydrochloric, hydriodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanilic, sulfonic, sulfuric, tannic, tartaric, and toluenesulfonic. In a preferred embodiment, the salt is hydrochloride salt.

The term "pharmaceutically acceptable salt" as used herein refers to acid addition salts or base addition salts of the compounds of the present invention, each such salt retaining the activity of the parent compound without imparting any deleterious or undesirable effect on a subject to whom it is administered and in the context in which it is administered, or which is recognized in the pharmaceutical sciences as a salt that is safe and effective when administered to a human as part of a pharmaceutical dosage form. Pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, citric, edetic, edisylic, estolic, esylic, formic, fumaric, glucceptic, gluconic, glutamic, glycolic, glycolylarsanilic, hexamic, hexylresorcinoic, hydrabamic, hydrobromic, hydrochloric, hydriodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanilic, sulfonic, sulfuric, tannic, tartaric, and toluenesulfonic. In a preferred embodiment, the pharmaceutically acceptable salt is hydrochloride salt.

The term "alkyl" as employed herein refers to both straight-chained and branched $C_1$-$C_{10}$ alkyl groups, preferably $C_1$-$C_4$ alkyl groups. Typical $C_1$-$C_{10}$ alkyl groups include methyl, ethyl, propyl, isopropyl, butyl, isobutyl, sec-butyl, tert-butyl, pentyl, isopentyl, neopentyl, hexyl, isohexyl, 3-methylpentyl, 2,2-dimethylbutyl, 2,3-dimethylbutyl, heptyl, 1-methylhexyl, 2-ethylhexyl, 1,4-dimethylpentyl, octyl, nonyl, and decyl. In a preferred embodiment, the alkyl is methyl.

The term "haloalkyl" as employed herein refers to an alkyl substituent as defined herein, wherein one or more hydrogen atoms are replaced with a halogen. Typical haloalkyl groups include chloromethyl, 1-bromoethyl, fluoromethyl, difluoromethyl, trifluoromethyl, trichloromethyl, and 1,1,1-trifluoroethyl, among others.

The term "cycloalkyl" as employed herein refers to a saturated cyclic alkyl containing from 3 to 10, preferably from 3 to 8, and most preferably from 3 to 6 carbon atoms. Examples of cycloalkyl groups include, but are not limited to, cyclopropyl, cyclobutyl, cyclopentyl, cyclohexyl, cycloheptyl, and cyclooctyl.

The term "aryl" as employed herein refers to monocyclic, bicyclic, or tricyclic aromatic groups containing from 6 to 14 carbons in the ring portion. Typical aryl groups include phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 3-amino-naphthyl, 2-methyl-3-amino-naphthyl, 6-amino-2-naphthyl, 4,6-dimethoxy-2-naphthyl, indanyl, biphenyl, phenanthryl, anthryl, and acenaphthyl.

The term "aralkyl" as employed herein refers to both straight-chained and branched $C_1$-$C_8$ alkyl groups having an aryl substituent, such as benzyl, phenylethyl, or 2-napthylmethyl, replacing a hydrogen atom.

Unless specifically indicated, references to "ritalinic acid" and "methylphenidate" include all four optical isomers of each compound, respectively. When a particular isomer is contemplated, that isomer is specifically indicated such as, for example, d-threo methylphenidate or l-threo methylphenidate. The combined threo isomers may be indicated simply as "threo" or as "dl-threo" ritalinic acid or "dl-threo" methylphenidate.

The process of the present invention includes, in various embodiments, reacting ritalinic acid or a salt thereof with methanol, with or without a co-solvent, in the presence of an acid catalyst. In a preferred embodiment, the methanol is dry methanol, or anhydrous methanol, preferably having a water content of less than 5% by weight, preferably less than 1% by weight, preferably less than 0.5% by weight, more preferably less than preferably less than 0.2% by weight, and even more preferably less than preferably less than 0.1% by weight.

equivalent of water per equivalent of ester formed. The esterification reaction is reversible and, under defined conditions, the reaction will reach an equilibrium. The equilibrium will be shifted toward the product by, for example, increasing the methanol concentration and/or removing water from the reaction mixture. However, increasing the water concentration during the reaction will result in shifting the equilibrium back toward the starting material and result in partial ester hydrolysis. Since water will shift the equilibrium toward the starting material, the reaction is preferably performed with anhydrous hydrogen chloride in methanol. However, anhydrous hydrogen chloride reacts with methanol and forms methyl chloride and water. The rate of this hydrogen chloride decomposition depends mainly on the reaction temperature and to a lesser extent, on the hydrogen chloride concentration; at higher temperatures, the decomposition rate increases and water is formed faster. Therefore, esterification reactions run at higher temperatures will result in an equilibrium shift—due to the additional water formed by decomposition of hydrogen chloride—toward the starting material and thus, will ultimately result over time in a lower conversion of ritalinic acid to methylphenidate compared to the reaction conducted a lower temperatures.

An excess amount of methanol is typically used in the reaction. In one embodiment, the ritalinic acid and methanol can be added together in a ratio of ritalinic acid:methanol in a range of from about 1:10 to about 1:100 molar equivalents, preferably from about 1:10 to about 1:55 molar equivalents, and more preferably from about 1:10 to about 1:38 molar equivalents. Other preferred embodiments use a ratio of ritalinic acid:methanol in a range of from about 1:20 to about 1:100 molar equivalents, preferably from about 1:20 to about 1:55 molar equivalents, and more preferably from about 1:20 to about 1:38 molar equivalents. In another Scheme 2

Scheme 3

The esterification of dl-threo and d-threo ritalinic acid is illustrated in Schemes 2 and 3, respectively. The first step, proton transfer, occurs very rapidly and is, under the acidic reaction conditions, irreversible. The second step, esterification with methanol, occurs under the formation of one embodiment, the ratio of ritalinic acid:methanol is about 1:15, 1:20, 1:25, 1:30, 1:35, or 1:45 molar equivalents.

In another embodiment, the ritalinic acid hydrochloride and methanol can be added together in a ratio of ritalinic acid hydrochloride:methanol in a range of from about 1:9 to about 1:86 molar equivalents, preferably from about 1:9 to about 1:47 molar equivalents, and more preferably from about 1:17 to about 1:33 molar equivalents. In another embodiment, the ratio of ritalinic acid hydrochloride:methanol is about 1:13, 1:17, 1:21, 1:30, 1:39, or 1:44 molar equivalents.

The acid catalyst is employed in an amount sufficient to catalyze the reaction. The acid catalyst may also serve as a dehydrating agent or desiccant for water produced as a by-product of the reaction. The acid catalyst may be an organic acid or an inorganic acid. Such acids include, but are not limited to sulfuric acid ($H_2SO_4$), phosphoric acid ($H_3PO_4$), hydrogen chloride (HCl), and hydrogen bromide (HBr). Preferred embodiments of the acid catalyst are hydrogen chloride or hydrogen bromide, wherein hydrogen chloride is the most preferred acid catalyst. The acid catalyst may be introduced by bubbling a gas such as HCl into the reaction mixture. The acid catalyst may also be generated in situ by the addition of an acid chloride such as thionyl chloride or acetyl chloride to an alcohol containing mixture prior to the addition of ritalinic acid or ritalinic acid hydrochloride. In view of the present disclosure, those skilled in the art will be familiar with these and other analogous acids that are capable of catalyzing the esterification reaction, but that do not chemically interfere with the reaction.

In one embodiment, the ritalinic acid and acid catalyst are added together in a ratio of ritalinic acid:acid catalyst in a range of from about 1:1.1 to about 1:9 molar equivalents, preferably about 1:2 to about 1:6 molar equivalents. In another embodiment, the ratio of ritalinic acid:acid catalyst is about 1:1.1, 1:2, 1:3, 1:4, 1:4.5, 1:5, 1:5.5, or 1:6 molar equivalents.

In another embodiment, the ritalinic acid hydrochloride and acid catalyst are added together in a ratio of ritalinic acid hydrochloride:acid catalyst in a range of from about 1:0.1 to about 1:8 molar equivalents, preferably about 1:1.7 to about 1:5.2 molar equivalents. In another embodiment, the ratio of ritalinic acid hydrochloride:acid catalyst is about 1:0.1, 1:1.7, 1:2.6, 1:3.4, 1:3.9, 1:4.3, 1:4.7, or 1:5.2 molar equivalents.

In some embodiments, the reaction mixture may include an additional non-reactive co-solvent that does not chemically interfere with the reaction. In certain embodiments, the co-solvent is selected from the group consisting of acetates, ketones, ethers, aromatic solvents, and higher alkanes, such as $C_{4-20}$ linear or branched alkanes, preferably $C_{5-10}$ linear or branched alkanes. Non-limiting examples of non-reactive co-solvents include methyl acetate, ethyl acetate, isopropyl acetate, n-butyl acetate, isobutyl acetate, acetone, methyl ethyl ketone, methyl isobutyl ketone, tetrahydrofuran, 2-methyltetrahydrofuran, acetonitrile, methyl t-butyl ether, dibutyl ether, cyclopentyl methyl ether, anisole, toluene, xylene, heptanes, and mixtures thereof. Preferred examples of non-reactive co-solvents include methyl acetate, ethyl acetate, isopropyl acetate, n-butyl acetate, isobutyl acetate, acetone, methyl ethyl ketone, methyl isobutyl ketone, dibutyl ether, anisole, toluene, heptanes, and mixtures thereof.

In one embodiment, the process of the present invention further comprises addition of an orthoester to the reaction mixture. The orthoester serves to remove water and hydrogen chloride from the reaction mixture thereby forming a stable mixture in which no additional water is formed from the reaction between HCl and methanol. In some embodiments, the orthoester is characterized by the formula $R^2C(OR^3)_3$ in which $R^2$ may be hydrogen or alkyl, preferably hydrogen or methyl, and $R^3$ may be alkyl, haloalkyl, cycloalkyl, aryl, or aralkyl, and preferably $C_1$-$C_4$ alkyl. In one embodiment, the orthoester is trimethyl orthoformate. In another embodiment, the orthoester is trimethyl orthoacetate.

In one embodiment, the orthoester can be added to the reaction mixture in a ratio of ritalinic acid:orthoester in a range of from about 1:1.1 to about 1:10 molar equivalents, preferably from about 1:1.1 to about 1:6 molar equivalents, more preferably from about 1:1.1 to about 1:4 molar equivalents, and even more preferably from about 1:1.1 to about 1:2.5 molar equivalents. In another embodiment, the ratio of ritalinic acid:orthoester is in a range of from about 1:1.8 to about 1:10 molar equivalents, preferably from about 1:1.8 to about 1:6 molar equivalents, more preferably from about 1:1.8 to about 1:4 molar equivalents, and even more preferably from about 1:1.8 to about 1:2.5 molar equivalents. In another embodiment, the ratio of ritalinic acid:orthoester is about 1:1.1, 1:1.5, 1:2, 1:3, 1:4, 1:4.5, 1:5, 1:5.5, or 1:6 molar equivalents.

In another embodiment, the orthoester can be added to the reaction mixture in a ratio of ritalinic acid hydrochloride:orthoester in a range of from about 1:0.1 to about 1:9 molar equivalents, preferably about 1:0.9 to about 1:5 molar equivalents. In another embodiment, the ratio of ritalinic acid hydrochloride:orthoester is about 1:0.1, 1:1.3, 1:1.7, 1:2.6, 1:3.4, 1:3.9, 1:4.3, 1:4.7, or 1:5 molar equivalents.

The amount of orthoester is in direct proportion to the amount of free acid catalyst, preferably HCl, at the start of the reaction. In one embodiment, the orthoester can be added to the reaction mixture in a ratio of acid catalyst:orthoester in a range of from about 1:0.8 to about 1:10 molar equivalents, preferably from about 1:0.8 to about 2 molar equivalents, more preferably from about 1:0.8 to about 1:2 molar equivalents. In another embodiment, the ratio of acid catalyst:orthoester is about 1:0.8, 1.1, 1:1.5, 1:2, 1:3, 1:4, 1:5, or 1.6 molar equivalents. In one embodiment, the orthoester can be added to the reaction mixture in a ratio of HCl:orthoester in a range of from about 1:0.8 to about 1:10 molar equivalents, preferably from about 1:0.8 to about 1:2 molar equivalents. In another embodiment, the ratio of HCl:orthoester is about 1:0.8, 1.1, 1:1.5, 1:2, 1:3, 1:4, 1:5, or 1.6 molar equivalents.

Figure 1:
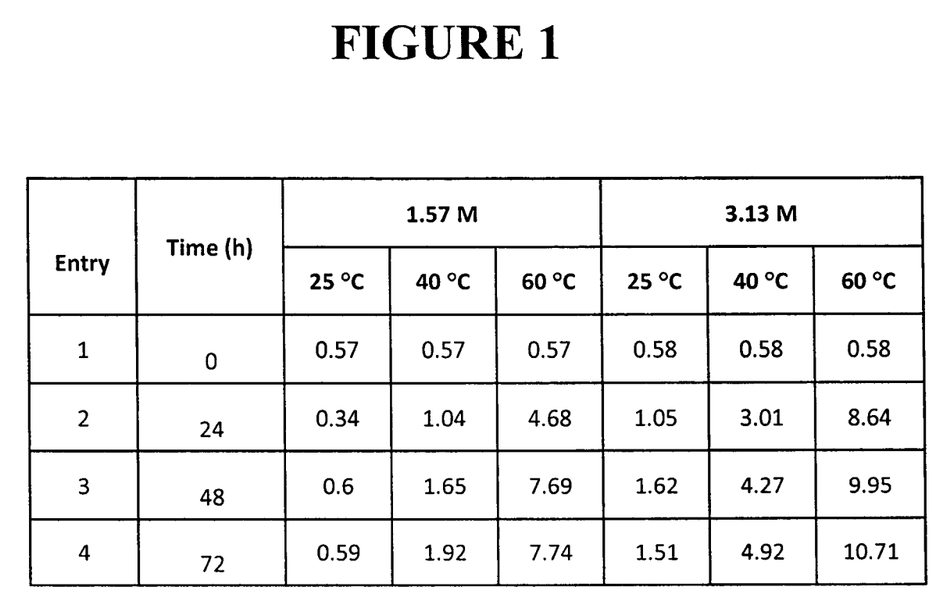
FIG. 1 provides the weight percentage of water of a 1.57 M and 3.13 M solution of hydrogen chloride in methanol at 25° C., 40° C., and 60° C. after 72 hours.

In the methylphenidate reaction, the decomposition of the hydrogen chloride to methyl chloride and water may affect the conversion rate. To further understand the decomposition process, a freshly prepared methanolic hydrogen chloride solution was monitored over a 24 hour period and the water content was determined by Karl Fischer titration (see FIG. 1). As shown in FIG. 1, after 72 hours at 60° C., the amount of water in a 3.13 M solution of hydrogen chloride in methanol was 10.7 wt % and the amount of water in a 1.57 M solution of hydrogen chloride in methanol was 7.7 wt %. This increase in water content is expected to cause a dramatic shift in the equilibrium back towards ritalinic acid. The effect is more profound at higher temperatures. In contrast, after 72 hours at 40° C., 4.9 wt % water was formed in a 3.13 M solution of hydrogen chloride in methanol and 1.92 wt % water was formed in a 1.57 M solution of hydrogen chloride in methanol. Furthermore, after 72 hours at 25° C., the water content was 1.5 wt % (3.13M) and 0.6% (1.57 M). Therefore, as demonstrated in FIG. 1, the amount of water formed depends on temperature and hydrogen chloride concentration; at a lower temperature, a higher hydrogen chloride concentration can be tolerated, and at a lower hydrogen chloride concentration, a higher temperature can be tolerated.

Since the water content is expected to affect the esterification equilibrium, it was hypothesized that at 40° C., the reaction might be slower, but should progress to a higher conversion rate compared to a reaction at 60° C. To test this hypothesis, two reactions were conducted at 40° C. and 60° C. under otherwise identical conditions.

Figure 2:
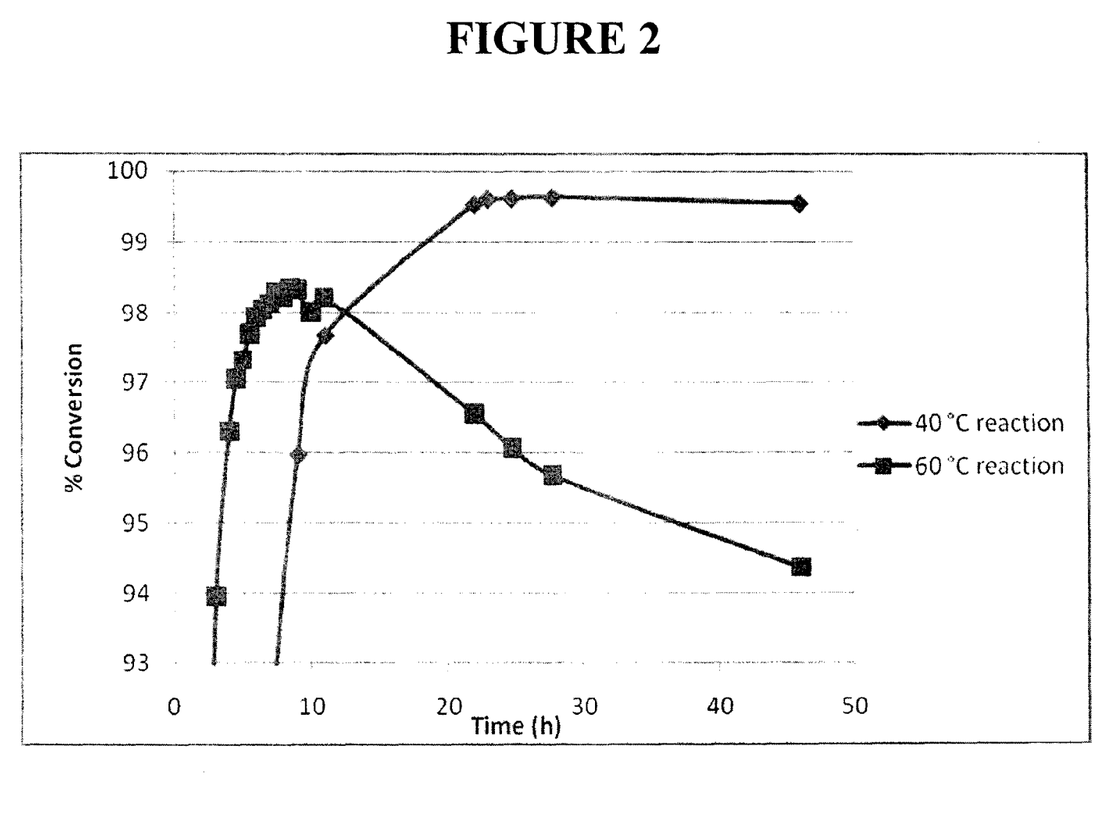
FIG. 2 is a graphical analysis of the esterification of ritalinic acid at 40° C. compared to the esterification of ritalinic acid at 60° C.

As shown in FIG. 2, the reaction that was run at 60° C. reached a maximum conversion rate after about five hours. After about five hours at 60° C., the conversion rate of the equilibrium reaction reversed because methylphenidate was being hydrolyzed at a faster rate than it was being formed. In contrast, the reaction that was run at 40° C. resulted in a 99% conversion that was stable for at least 50 hours. As discussed above, the reaction carried out at 60° C. results in the formation of more water due to the degradation of hydrogen chloride in methanol (to form water and methyl chloride), resulting in a shift in the equilibrium of the reaction away from the desired product.

Since production on a commercial scale may entail extended hold and process times of up to several days, it is highly desirable to use a process that results in a reaction mixture achieving and retaining a high conversion rate that remains stable when the reaction is run or the product is held over an extended period of time. Furthermore, a high conversion rate (for example >98%) reduces the need for additional steps to purify the product. The addition of a purification step not only lowers the yield, but also adds process steps and times, which can significantly increase costs when performed on a large scale.

The rate of the esterification reaction depends on the reaction temperature and on the hydrogen chloride concentration; at higher temperatures and higher hydrogen chloride concentration, the reaction rate increases. Conversely, esterification reactions run at lower temperatures will result in a slower reaction rate.

At higher temperatures (>50° C.), the reaction rate is high, but the mixture formed is not stable over an extended period of time (for example, about 48 to about 144 hours), whereas at lower temperatures (<10° C.), the reaction mixture is stable over an extended period of time, but progresses at a very slow reaction rate.

Under preferred process conditions, the reaction rate is fast enough to minimize the process time while keeping the ester hydrolysis at a rate low enough to compensate for the potential process delays.

In general, the reaction conditions include reacting at a temperature of less than 45° C., or less than 43° C., or less than 42° C., or less than 40° C. The reaction conditions may also include a temperature from about 0° C. to less than 45° C., or from about 5° C. to less than 45° C., or from about 5° C. to about 40° C., or from about 10° C. to less than 45° C., or from about 10° C. to about 43° C., or from about 10° C. to about 40° C., or from about 20° C. to less than 45° C., or from about 20° C. to about 43° C., or from about 20° C. to about 40° C., or from about 10° C. to about 30° C., or from about 20° C. to about 30° C., or from about 30° C. to less than 45° C., or from about 30° C. to about 43° C., or from about 30° C. to about 40° C.

As seen in FIG. 1, the reaction temperature and the concentration of HCl are interrelated. In one embodiment, the reaction temperature is from about 5° C. to about 15° C., and the HCl concentration is from about 4 M to about 10 M, or from about 5° C. to about 40° C., and the HCl concentration is from about 1.3 M to about 10 M.

In another embodiment, the reaction temperature is from about 15° C. to about 25° C., and the HCl concentration is from about 3 M to about 8 M, or from about 20° C. to about 40° C., and the HCl concentration is from about 2 M to about 6 M.

In another embodiment, the reaction temperature is from about 25° C. to about 35° C., and the HCl concentration is from about 2 M to about 6 M, or from about 10° C. to about 30° C., and the HCl concentration is from about 3 M to about 10 M.

In another embodiment, the reaction temperature is from about 35° C. to about 45° C., and the HCl concentration is from about 1.3 M to about 5 M, or from about 20° C. to about 30° C., and the HCl concentration is from about 3 M to about 6 M.

In another embodiment, the reaction temperature is from about 30° C. to about 40° C., and the HCl concentration is from about 1.3 M to about 6 M, and preferably from about 2 M to about 6 M.

The reaction may proceed for any length of time necessary to achieve conversion of ritalinic acid or a salt thereof to methylphenidate or a salt thereof. In one embodiment, the reaction proceeds for about 0.5 to about 100 hours. In another embodiment, the reaction proceeds for about 4 to about 72 hours. In another embodiment, the reaction proceeds for about 6 to about 48 hours. In another embodiment, the reaction proceeds for about 15 to about 30 hours.

Figure 3A:
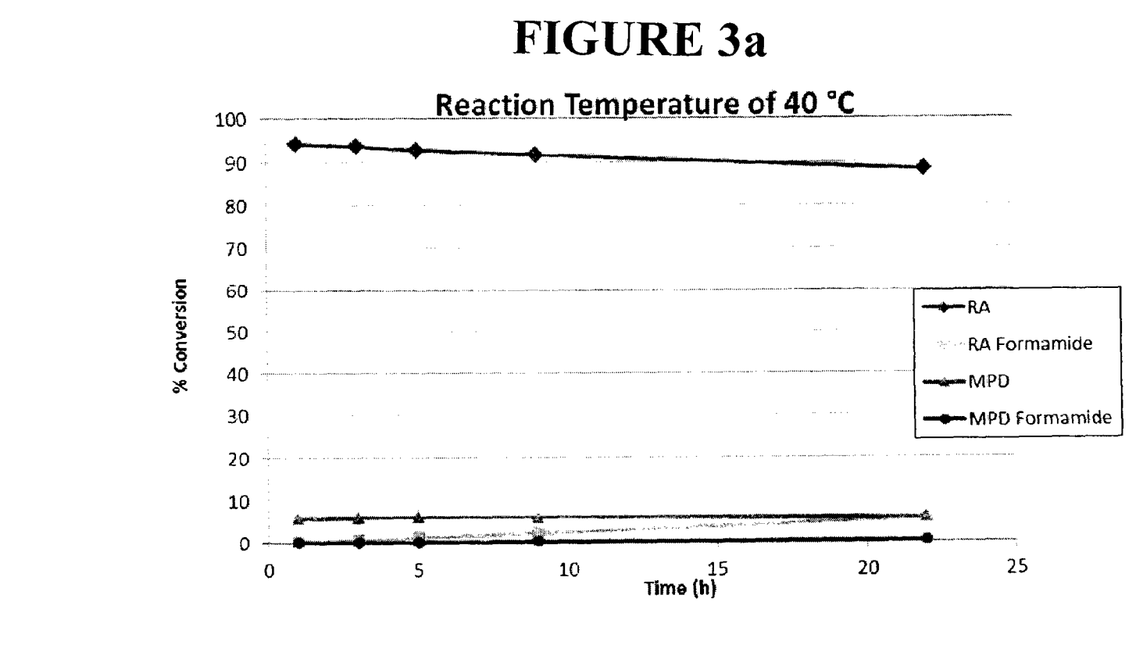
FIG. 3 is a graphical analysis of the esterification of ritalinic acid (RA) to methylphenidate (MPD) when trimethyl orthoformate is added at the beginning of the reaction (a) at 40° C. and (b) at 60° C.
Figure 3B:
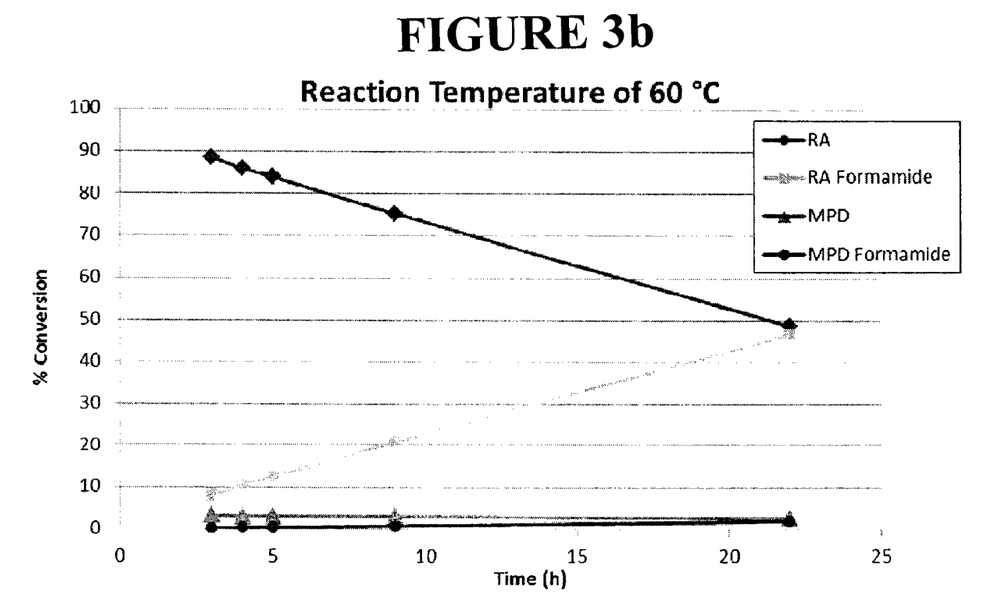

In another aspect of the invention, it has been unexpectedly determined that the addition of an orthoester at the beginning of the esterification reaction inhibits the conversion to methylphenidate. The orthoester will react not only with the water that is formed, but also with the acid catalyst. Therefore, addition of an orthoester at the beginning of the reaction removes acid catalyst from the reaction. FIG. 3 shows the results of the addition of trimethyl orthoformate at the beginning of the reaction when the reaction is run at (a) 40° C. versus (b) 60° C. As demonstrated, the reactions with trimethyl orthoformate added at the beginning of the reaction showed very little conversion at either temperature, and additional side products were generated at 60° C.

Scheme 4 ritalinic acid hydrochloride (R = H)
methylphenidate hydrochloride (R = CH₃)

ritalinic acid hydrochloride (R = H)
methylphenidate hydrochloride (R = CH₃)

Side products generated in the esterification of ritalinic acid with trimethyl orthoformate (TMOF) or trimethyl orthoacetate (TMOA) are illustrated in Scheme 4. Use of an excess amount of orthoester in relation to the amount of ritalinic acid will allow the excess orthoester to react with either the methylphenidate formed (if added at the end of the reaction) or with the ritalinic acid (if added at the beginning of the reaction). The side products formed will decrease the yield and may also result in the need for additional purification steps.

To overcome this problem, the orthoester is preferably added after the reaction has commenced. In one embodiment, the orthoester is added to the reaction mixture after the reaction has proceeded for about 0.2 to about 50 hours. In another embodiment, the orthoester is added to the reaction mixture after the reaction has proceeded for about 0.5 to about 25 hours. In another embodiment, the orthoester is added to the reaction mixture after the reaction has proceeded for about 3 to about 20 hours, and preferably after the reaction has proceed for about 20 hours.

In certain embodiments, after addition of the orthoester, the reaction is allowed to proceed for about 0.2 to about 120 hours, or for about 0.5 to about 25 hours, or for about 1.0 to about 20 hours, or for about 3 to about 10 hours, or for about 2 to about 24 hours.

In another embodiment, the orthoester is added to the reaction mixture after the reaction has reached about 90% conversion, or about 95% conversion, or about 98% conversion, or about 99% conversion, or about 99.1% conversion to form methylphenidate or the methylphenidate salt. Methods for determining the percent conversion to methylphenidate or the methylphenidate salt are known in the art and include, e.g., the use of high-performance liquid chromatography (HPLC).

After the addition of the orthoester, the mixture may be polish filtered to remove any insoluble particulates.

Following the esterification process, methylphenidate or a methylphenidate salt may be isolated from the reaction mixture by conventional methods known in the art in view of this disclosure. In some embodiments, isolation of methylphenidate may involve precipitation or crystallization of the crude product. This may be achieved by any method known in the art such as, for example, by cooling the product mixture sufficiently to precipitate the methylphenidate or methylphenidate salt, or by adding a solvent (i.e., an "anti-solvent") in which methylphenidate or salt thereof has reduced solubility, or by partial or complete exchange of methanol in the product mixture with a solvent in which methylphenidate or salt has reduced solubility, or a combination of such methods. Further steps of purification may also be performed such as, for example, recrystallization.

In one embodiment, methylphenidate or salt thereof is isolated from the product mixture after addition of the orthoester using partial solvent exchange. In certain embodiments, the solvent (anti-solvent) is selected from the group consisting of acetates, ketones, ethers, aromatic solvents, and higher alkanes, such as $C_{4-20}$ linear or branched alkanes, preferably $C_{5-10}$ linear or branched alkanes. Non-limiting examples of suitable solvents (anti-solvents) for solvent exchange include ethanol, isopropanol, n-propanol, n-butanol, iso-butanol, t-amyl alcohol, cyclopentanol, methyl acetate, ethyl acetate, isopropyl acetate, n-propyl acetate, n-butyl acetate, isobutyl acetate, acetone, methyl ethyl ketone, methyl isobutyl ketone, tetrahydrofuran, 2-methyltetrahydrofuran, acetonitrile, diethyl ether, methyl-t-butyl ether, dibutyl ether, cyclopentyl methyl ether, anisole, toluene, xylene, hexanes, heptanes, and mixtures thereof. Preferred solvents include ethanol, isopropanol, methyl acetate, ethyl acetate, isopropyl acetate, n-butyl acetate, isobutyl acetate, acetone, methyl ethyl ketone, methyl isobutyl ketone, dibutyl ether, anisole, toluene, heptanes, and mixtures thereof. After addition of a suitable solvent, all or a portion of the remaining methanol can be removed from the reaction mixture. Methanol may be removed by distillation at atmospheric pressure or under reduced pressure. In one embodiment, methanol is removed at atmospheric pressure at about 70° C. In another embodiment, methanol is removed at reduced pressure at about 40° C. The anti-solvent can be added concurrently during the distillation process or after a portion of methanol has already been removed. The distillation process may be carried out once, or repeated several times, or the product can be isolated directly after the addition of the anti-solvent.

A methylphenidate salt as present in the product mixture can be converted to methylphenidate free base using conventional methods known in the art. Methylphenidate free base can in turn be converted to a pharmaceutically acceptable salt of methylphenidate using conventional methods known in the art.

Methylphenidate and pharmaceutically acceptable salts thereof, made by the present invention, may be administered to a subject in need of such treatment by any standard route including oral, oromucosal, buccal, transdermal, intranasal, sublingual, vaginal, rectal, parenteral, or topical routes. Methylphenidate and the pharmaceutically acceptable salts thereof, produced according the processes of the invention, may be administered to subjects to treat conditions known in the art to be treatable by administration of methylphenidate or its pharmaceutically acceptable salts, including attention deficit hyperactivity disorder (ADHD) and narcolepsy. Methylphenidate and the pharmaceutically acceptable salts thereof may be administered in dosages and according to dosing regimens known in the art. Dosages may range from about 0.01 mg to about 75 mg per day. In one embodiment, methylphenidate or a pharmaceutically acceptable salt thereof may be administered in a dosage of 5, 10, or 20 mg per day in single or divided doses. In another embodiment, a dosage level that is in the range of about 0.001 mg to about 10 mg per kg of body weight per day is employed. Variations in dosages may nevertheless occur depending upon the age, weight, and condition of the subject being treated, his or her individual response to the medicament, on the type of pharmaceutical formulation and route of administration chosen, and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

Methylphenidate and pharmaceutically acceptable salts thereof, made by the present invention, may be administered alone or in combination with one or more pharmaceutically acceptable carriers or diluents by any of the several routes previously indicated. More particularly, the methylphenidate and pharmaceutically acceptable salts thereof may be administered in any of a wide variety of different dosage forms, and these may comprise any of various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, among other forms. Such carriers may include solid diluents or fillers, sterile aqueous media and various non-toxic organic solvents. Oral pharmaceutical compositions can be suitably sweetened and/or flavored. In general, the methylphenidate and pharmaceutically acceptable salts thereof, are present in such a dosage form at a concentration level ranging from about 5% to about 70% by weight.

Methylphenidate and pharmaceutically acceptable salts thereof, made by the present invention, may also be administered in combination with another active agent.

EXAMPLES

Having now generally described this invention, the same will be understood by reference to the following examples which are provided herein for purposes of illustration only and are not intended to be limiting unless otherwise specified.

Example 1

Synthesis of dl-threo methylphenidate hydrochloride with hydrogen chloride, trimethyl orthoformate, and isopropanol as anti-solvent at 41-42° C.:

To 60.88 g dl-threo ritalinic acid was added methanol (200 mL) and HCl gas (30.4 g, 3.0 eq) as the HCl source. After 20 hours at 41-42° C., conversion as determined by HPLC was 99.1%. Trimethyl orthoformate (2.0 eq) was added in one portion. After 3.5 hours at 41-42° C. and 19 hours at room temp, the reaction mixture supernatant was 0.34% water as measured by Karl Fischer titration. The conversion as determined by HPLC was 99.8%. The product mixture was distilled at 19.9-21.3 kPa (150-160 torr) while isopropanol (200 mL) was simultaneously added. The boiling point was 37-39° C. while the pot temperature was 40-43° C. 190 mL of distillate was collected over 3.5 hours. The reaction mixture was cooled to 2° C. for 30 minutes, filtered, and washed with isopropanol (3×75 mL). The solid from the filtration was dried at 60° C. to afford dl-threo methylphenidate hydrochloride as a white solid (68.99 g, 92.0% yield). HPLC analysis showed a purity of >99.9%. The resulting reaction mixture was stable (greater than 99% conversion) for more than 50 hours.

Example 2

Synthesis of dl-threo methylphenidate hydrochloride using the process of Example 1 at 20° C. instead of 41-42° C. The resulting reaction mixture was stable (greater than 99% conversion) for more than 6 days.

Example 3

Synthesis of dl-threo methylphenidate hydrochloride using the process of Example 1 with 5 equivalents of hydrogen chloride instead of 3 equivalents and at 20° C. instead of 41-42° C. The resulting reaction mixture was stable (greater than 99% conversion) for more than 6 days.

Example 4

Synthesis of dl-threo methylphenidate hydrochloride using the process of Example 1 with 6 equivalents of hydrogen chloride instead of 3 equivalents and at 20° C. instead of 41-42° C. The resulting reaction mixture was stable (greater than 99% conversion) for more than 6 days.

Example 5

Synthesis of dl-threo methylphenidate hydrochloride using the process of Example 1 with 2 equivalents of hydrogen chloride instead of 3 equivalents and at 30° C. instead of 41-42° C. The resulting reaction mixture was stable (greater than 99% conversion) for more than 6 days.

Example 6

Synthesis of dl-threo methylphenidate hydrochloride using the process of Example 1 with 6 equivalents of hydrogen chloride instead of 3 equivalents of hydrogen and at 30° C. instead of 41-42° C. The resulting reaction mixture was stable (greater than 99% conversion) for more than 6 days.

Example 7

Synthesis of dl-threo methylphenidate hydrochloride with hydrogen chloride, trimethyl orthoformate, and isopropanol as anti-solvent at 19-20° C.:

Dry methanol (250 mL) was charged with hydrogen chloride gas (33.85 g) at 20-25° C. The solution was diluted with methanol (50 mL) and charged with dl-threo ritalinic acid (50.88 g, 4 eq). After stirring 5 days at 19-20° C., conversion as determined by HPLC was 99.86%. Trimethyl orthoformate (76 mL, 3 eq) was added and the reaction was heated 2 hours at 40° C. Vacuum distillation was carried out at 19.9-26.7 kPa (150-200 torr), with a pot temperature of 38-42° C. The distillate was collected in three fractions, charging 100 mL of dry isopropanol between each fraction. The reaction mixture was cooled to 20° C., filtered, and washed with isopropanol (2×100 mL). The resulting white solid was dried in a vacuum drying oven at room temperature overnight to afford dl-threo methylphenidate hydrochloride as a white crystalline solid (58.77 g, 93.9% yield, 99.98% HPLC purity).

Example 8

Synthesis of dl-threo methylphenidate hydrochloride with hydrogen chloride, trimethyl orthoformate, and toluene as anti-solvent at 41-42° C.:

To 50.47 g of dl-threo ritalinic acid was added methanol (200 mL) and HCl gas (25.2 g, 3 eq) as the HCl source. After 20 hours at 41-42° C., conversion by HPLC was 99.1%. Trimethyl orthoformate (2 eq) was added in one portion. After 1 hour at 41-42° C., the supernatant was 0.09% water as measured by Karl Fischer titration. The conversion as determined by HPLC was 99.5%. The reaction was allowed to stir an additional hour at 41-42° C. The reaction mixture was distilled at 29.3-30.6 kPa (220-230 torr) while toluene (200 mL) was simultaneously added. The boiling point was 37-39° C. while the pot temperature was 39-41° C. 210 mL of distillate was collected over 2.5 hours. The distillate was 4.56:1 mol:mol (61:39 wt %) methanol:toluene by $^1$H NMR analysis. The reaction mixture was cooled to 2° C. for 1 hour, filtered, and washed with toluene (3×50 mL). The filtrate (344 mL total) was biphasic, with about 10 mL of an orange bottom layer. The top layer was toluene with a trace of methanol by $^1$H NMR. The bottom layer was 5:1 mol:mol methanol:toluene with traces of product. The solid was dried at 60° C. to afford a white solid (51.09 g, 91.5% yield). HPLC analysis showed a purity of 99.8%. The filtrate (bottom layer) showed 99.5:0.5 methylphenidate:ritalinic acid with toluene and other trace impurities.

Example 9

Synthesis of dl-threo methylphenidate hydrochloride with acetyl chloride/methanol at 42-44° C.:

Acetyl chloride (137 mmol) was added into methanol (35 mL). Dl-threo ritalinic acid (10.0 g, 45.6 mmol) was added and the reaction was heated at 42-44° C. for 20 hours. HPLC showed >99% conversion. Dilution with methanol, distillation, and cooling yielded 10.86 g (88%) dl-threo methylphenidate hydrochloride with 99.8% purity.

Example 10

Comparison of the esterification process at 40° C. and 55° C.:

Two 10 mL aliquots of the reaction mixture of Example 1 were removed after 2 hours of heating. The aliquots were heated on a reaction block in sealed vials. The first was a control at 40° C. The second was heated at 55° C. After 2 hours, the conversion of the vial heated to 40° C. was 87.6%; the conversion of the vial heated to 55° C. was 94.6%. After 20 hours, conversion of the vial heated to 40° C. was 99.5%; the conversion of the vial heated to 55° C. was 97.8%. The vial heated to 55° C. had significant pressure built up (MeCl formation) when it was opened after 20 hours. Table 1 compares the conversion to methylphenidate for the reactions run at 40° C. and 55° C. As shown in Table 1, the 55° C. reaction, although initially faster, resulted in a lower maximum conversion than the reaction run at 40° C. after 20 hours.

TABLE 1

Conversion to methylphenidate at 40° C. and 55° C.

| Time | 40° C. (% conversion) | 55° C. (% conversion) |
| --- | --- | --- |
| 2 hours | 87.6 | 94.6 |
| 20 hours | 99.5 | 97.8 |

Example 11

Comparison of the esterification process at 40° C. and 60° C.:

A 4.6 M methanolic HCl solution was prepared by adding gaseous HCl into methanol affording a stock solution containing 17.55 wt % of HCl and 0.06 wt % of water as measured by Karl Fischer titration. Four 20 mL vials were charged with 12 mL of this stock solution. Two vials were charged with 4.04 g (0.184 mol) of ritalinic acid and two vials were used as blanks. One vial with ritalinic acid and one blank were heated to 40° C. and the other two vials were heated to 60° C. As shown in FIG. 2, the 60° C. reaction, although faster, resulted in a lower maximum conversion than the reaction at 40° C. By HPLC, the 60° C. reaction reached a maximum conversion of about 98.5% after about 9 hours. Then the conversion dropped, due to increasing ester hydrolysis, to about 94% after 48 hours. The 40° C. reaction reached a maximum conversion of about 99.6% after about 24 hours and showed only minimal ester hydrolysis over the next 24 hours, ending with 99.5% conversion.

Example 12

Effect of addition of trimethyl orthoformate at beginning of reaction:

A 4.6 M methanolic HCl solution was prepared by adding gaseous HCl into methanol affording a stock solution containing 17.55 wt % of HCl and 0.06 wt % of water measured by Karl Fischer titration. Four 20 mL vials were charged with 8 mL of this stock solution. Two vials were charged with 2.69 g (0.123 mol) of ritalinic acid and two vials were used as blanks. One vial with ritalinic acid and one blank were heated to 40° C. and the other two vials were heated to 60° C. As shown in FIG. 3, the reactions with trimethyl orthoformate added at the beginning of the reaction showed very little conversion at either temperature. The small amount of conversion may have occurred in the short time period prior to the addition of the trimethylorthoformate. An undesired side reaction, the reaction of ritalinic acid and methylphenidate with trimethyl orthoformate to form formamides, was observed, especially in the 60° C. reaction.

Example 13

Effect of addition of trimethyl orthoformate at beginning of reaction:

Addition of trimethyl orthoformate (TMOF) at the start of the reaction was evaluated with 1.25, 2.5, and 5.0 equivalents of TMOF based on the amount of ritalinic acid. Trimethyl orthoformate was added to a reaction mixture comprising 2.1 equivalents of HCl (concentration at 3 mL/g) and a temperature of 40° C. As seen in Table 2, after 24 hours, conversion was 64% using 1.25 equivalents of TMOF and 8% for both 2.5 and 5.0 equivalents of TMOF. The results showed that addition of TMOF at the beginning of the reaction led to a drastic inhibition of the esterification reaction. This indicated that HCl was reacting with the TMOF resulting in a loss of HCl as a reagent in the reaction. With less HCl present, the esterification reaction slowed down considerably.

TABLE 2

Conversion to methylphenidate with trimethyl orthoformate added at beginning of reaction.

| eq. TMOF | Conversion after 24 h |
| --- | --- |
| 0 | >95% |
| 1.25 | 64% |
| 2.5 | 8% |
| 5.0 | 8% |

Example 14

Synthesis of dl-threo methylphenidate hydrochloride with hydrogen chloride, trimethyl orthoacetate, and isopropanol as anti-solvent with polish filtration:

Dry methanol (234.6 mL) was charged with hydrogen chloride (26.74 g). The solution was diluted with methanol (85.5 mL) and charged with 53.61 g of dl-threo ritalinic acid (3 equivalents of HCl in 6 volumes of methanol). After stirring for 21.5 hours at 40° C., conversion as determined by HPLC was >99.00%. Trimethyl orthoacetate (61.5 mL, 2 eq) was charged over ten minutes and complete dissolution was achieved in 5 minutes. After two hours of stirring at 40° C., the mixture was polish filtered, rinsed with 30 mL methanol, and charged back into a clean reaction vessel. HPLC showed 99.35% conversion. Vacuum distillation was carried out over 3.5 hours at 19.9 kPa (150 torr), with a pot temperature of 38-42° C. The distillate was collected in three fractions, charging 107 mL isopropanol between each fraction. After stirring overnight at ambient temperature, the reaction mixture was cooled to 2-5° C. for 60 minutes, filtered, and washed with isopropanol (2×100 mL). The material was dried at 60° C. in a vacuum oven for 2.5 hours to afford a white crystalline solid of dl-threo methylphenidate hydrochloride (61.09 g, 92.6%, 99.90% HPLC purity).

Example 15

Synthesis of d-threo methylphenidate hydrochloride with hydrogen chloride, trimethyl orthoformate, and isopropanol as anti-solvent:

Dry methanol (200 mL) was charged with hydrogen chloride (13.6 g, 373 mmol, 2.2 eq) at 20-25° C. over 15 minutes. To this solution was added d-threo ritalinic acid hydrochloride (43.2 g, 169 mmol, 1.0 eq) in one portion, followed by additional methanol (23 mL, 6 volumes total methanol based on free base). The reaction was heated at 35° C. for 27 hours, at which time the conversion by HPLC was 98.81%. After 28 h, trimethyl orthoformate (40.7 mL, 372 mmol, 2.2 eq) was added and the reaction was allowed to stir 1 hour at 40° C. The reaction mixture was distilled in vacuo (119 mL distillate collected) and isopropanol (100 mL) was added. The reaction mixture was distilled further (65 mL distillate collected), and isopropanol (95 mL) was added. The reaction mixture was distilled further (25 mL distillate collected), and cooled to room temperature. After stirring at room temperature for 3 days, the slurry was cooled to 2° C., filtered, washed with cold (<10° C.), isopropanol (2×100 mL), and dried to afford enantiopure d-threo methylphenidate HCl as a white solid (43.19 g, 94.7% yield, 99.73% HPLC purity).

Having now fully described this invention, it will be understood by those of ordinary skill in the art that the same can be performed within a wide and equivalent range of conditions, formulations and other parameters without affecting the scope of the invention or any embodiment thereof. All patents, patent applications, and publications cited herein are fully incorporated by reference herein in their entirety.

What is claimed is:

1. A method for the preparation of methylphenidate or a salt thereof, which comprises:
    reacting:
    (a) ritalinic acid or a salt thereof; and
    (b) methanol;
    (c) in the presence of an acid catalyst; and
    (d) adding, after commencing said reacting, an orthoester of the formula $R^2C(OR^3)_3$, wherein
        $R^2$ is hydrogen or alkyl; and
        $R^3$ is selected from the group consisting of alkyl, haloalkyl, cycloalkyl, aryl, and aralkyl;
    in a reaction mixture at a reaction temperature less than 45° C. to obtain a product mixture comprising methylphenidate or a salt thereof.

2. The method of claim 1, wherein the salt of ritalinic acid is threo ritalinic acid hydrochloride.

3. The method of claim 1, wherein the salt of methylphenidate is threo methylphenidate hydrochloride.

4. The method of claim 1, wherein the acid catalyst is an organic acid or an inorganic acid.

5. The method of claim 1, wherein the acid catalyst is selected from the group consisting of sulfuric acid ($H_2SO_4$), phosphoric acid ($H_3PO_4$), hydrogen chloride (HCl), and hydrogen bromide (HBr).

6. The method of claim 1, wherein the acid catalyst is hydrogen chloride.

7. The method of claim 1, wherein the reaction temperature is less than 43° C.

8. The method of claim 1, wherein the ratio of ritalinic acid:methanol is about 1:10 to about 1:100 molar equivalents.

9. The method of claim 2, wherein the ratio of ritalinic acid hydrochloride:methanol is about 1:9 to about 1:86 molar equivalents.

10. The method of claim 1, wherein the ratio of ritalinic acid:acid catalyst is about 1:1.1 to about 1:9 molar equivalents.

11. The method of claim 2, wherein the ratio of ritalinic acid hydrochloride:acid catalyst is about 1:0.1 to about 1:8 molar equivalents.

12. The method of claim 1, wherein $R^3$ is methyl.

13. The method of claim 1, wherein the orthoester is trimethyl orthoformate.

14. The method of claim 1, wherein the orthoester is trimethyl orthoacetate.

15. The method of claim 1, wherein said reacting occurs in the presence of a co-solvent.

16. The method of claim 15, wherein the co-solvent is selected from the group consisting of acetates, ketones, ethers, aromatic solvents, and linear or branched $C_{4-20}$ alkanes.

17. The method of claim 15, wherein the co-solvent is selected from the group consisting of methyl acetate, ethyl acetate, n-propyl acetate, isopropyl acetate, n-butyl acetate, isobutyl acetate, acetone, methyl ethyl ketone, methyl isobutyl ketone, tetrahydrofuran, 2-methyltetrahydrofuran, acetonitrile, diethyl ether, methyl t-butyl ether, dibutyl ether, cyclopentyl methyl ether, anisole, toluene, xylene, hexanes, heptanes, and mixtures thereof.

18. The method of claim 1, wherein the orthoester is added after about 95% conversion of the ritalinic acid or salt thereof to the methylphenidate or the salt thereof.

19. The method of claim 1, wherein the orthoester is added after 98% conversion of the ritalinic acid or salt thereof to the methylphenidate or the salt thereof.

20. The method of claim 1, wherein the orthoester is added after 99% conversion of the ritalinic acid or salt thereof to the methylphenidate or the salt thereof.

21. The method of claim 1, wherein the ratio of ritalinic acid:orthoester is from about 1:1.1 to about 1:10 molar equivalents.

22. The method of claim 1, wherein the ratio of ritalinic acid hydrochloride:orthoester is from about 1:0.1 to about 1:9 molar equivalents.

23. The method of claim 1, wherein the acid catalyst is HCl and wherein the ratio of HCl:orthoester is from about 1:0.8 to about 1:10 molar equivalents.

24. The method of claim 1, wherein the acid catalyst is HCl and wherein the ratio of HCl:orthoester is from about 1:0.8 to about 1:2 molar equivalents.

25. The method of claim 1, further comprising isolating said methylphenidate or salt thereof from the product mixture.

26. The method of claim 25, wherein said isolating is carried out (i) by cooling the product mixture, (ii) by adding a solvent in which the methylphenidate or methylphenidate salt has reduced solubility to the product mixture, (iii) by removal of at least a portion of the methanol from the product mixture, (iv) by adding a crystallization seed to the product mixture, or (v) by a combination of any of (i) to (iv).

27. The method of claim 26, wherein said isolating comprises adding a solvent in which the methylphenidate or salt thereof has reduced solubility to the product mixture so as to cause the methylphenidate or salt thereof to precipitate out of solution.

28. The method of claim 27, wherein the solvent is selected from the group consisting of ethanol, isopropanol, n-propanol, isobutanol, n-butanol, t-amyl alcohol, cyclopentanol, acetates, ketones, ethers, aromatic solvents, and linear or branched $C_{4-20}$ alkanes.

29. The method of claim 27, wherein said solvent is selected from the group consisting of ethanol, isopropanol, n-propanol, isobutanol, n-butanol, t-amyl alcohol, cyclopentanol, methyl acetate, ethyl acetate, n-propyl acetate, isopropyl acetate, n-butyl acetate, isobutyl acetate, acetone, methyl ethyl ketone, methyl isobutyl ketone, tetrahydrofuran, 2-methyltetrahydrofuran, acetonitrile, diethyl ether, methyl-t-butyl ether, dibutyl ether, cyclopentyl methyl ether, anisole, toluene, xylene, hexanes, heptanes, and mixtures thereof.

30. The method of claim 27, which further comprises:
removing at least a portion of the methanol from the product mixture simultaneous with adding said solvent.

31. The method of claim 27, which further comprises:
removing at least a portion of the methanol from the product mixture prior to adding said solvent.

32. The method of claim 1, wherein the reaction temperature is from about 35° C. to about 45° C., and the HCl concentration is from about 1.3 M to about 5 M.

33. The method of claim 6, wherein the hydrogen chloride is generated in situ by the addition of thionyl chloride or acetyl chloride.

* * * * *